United States Patent
Knittel et al.

(10) Patent No.: US 8,573,187 B2
(45) Date of Patent: Nov. 5, 2013

(54) APPARATUS FOR MEASURING A HYDROCARBON CONCENTRATION AND INTERNAL COMBUSTION ENGINE

(75) Inventors: Thorsten Knittel, Regensburg (DE); Andreas Wildgen, Nittendorf (DE)

(73) Assignee: Continental Automobile GmbH, Hannover (DE)

( * ) Notice: Subject to any disclaimer, the term of this patent is extended or adjusted under 35 U.S.C. 154(b) by 329 days.

(21) Appl. No.: 13/061,798

(22) PCT Filed: Sep. 2, 2009

(86) PCT No.: PCT/EP2009/061306
§ 371 (c)(1),
(2), (4) Date: Mar. 2, 2011

(87) PCT Pub. No.: WO2010/026146
PCT Pub. Date: Mar. 11, 2010

(65) Prior Publication Data
US 2011/0168139 A1 Jul. 14, 2011

(30) Foreign Application Priority Data
Sep. 2, 2008 (DE) .......................... 10 2008 045 322

(51) Int. Cl.
*F02M 33/02* (2006.01)
(52) U.S. Cl.
USPC .......................... 123/518; 123/557; 73/114.39
(58) Field of Classification Search
USPC ............ 123/518, 556, 557; 73/23.31, 114.34, 73/114.39, 114.71
See application file for complete search history.

(56) References Cited

U.S. PATENT DOCUMENTS

| | | | |
|---|---|---|---|
| 4,817,414 A | 4/1989 | Hagen et al. | |
| 5,535,614 A | 7/1996 | Okamoto et al. | |
| 6,227,177 B1 * | 5/2001 | Yamafuji et al. | 123/520 |
| 6,237,575 B1 * | 5/2001 | Lampert et al. | 123/520 |
| 6,638,406 B2 * | 10/2003 | Taniguchi | 204/424 |
| 6,662,121 B1 | 12/2003 | Oda et al. | |
| 6,895,802 B2 | 5/2005 | Stark et al. | |
| 7,188,519 B2 * | 3/2007 | Hornung et al. | 73/204.26 |
| 7,603,990 B2 * | 10/2009 | Takakura et al. | 123/520 |
| 7,690,364 B2 | 4/2010 | Grunwald et al. | |
| 7,755,466 B2 * | 7/2010 | Beck et al. | 338/25 |
| 8,312,868 B2 * | 11/2012 | Bierl et al. | 123/518 |
| 2005/0211228 A1 | 9/2005 | Amano et al. | |
| 2010/0186482 A1 | 7/2010 | Bierl et al. | |
| 2011/0174276 A1 * | 7/2011 | Bierl et al. | 123/518 |

FOREIGN PATENT DOCUMENTS

| | | |
|---|---|---|
| CN | 1673505 A | 9/2005 |
| DE | 30 47 601 A1 | 7/1982 |
| DE | 36 22 307 C2 | 8/1988 |
| DE | 42 44 224 | 6/1994 |
| DE | 42 44 224 A1 | 6/1994 |
| DE | 195 09 310 | 9/1996 |
| DE | 102 51 130 B4 | 4/2005 |
| DE | 10 2005 022 121 B3 | 11/2006 |
| DE | 10 2006 059 566 A1 | 6/2008 |
| DE | 10 2007 033 144 A1 | 1/2009 |
| EP | 1 094 306 | 4/2001 |
| EP | 1 094 306 A1 | 4/2011 |
| JP | 2000 065783 | 3/2003 |

* cited by examiner

*Primary Examiner* — Hai Huynh
(74) *Attorney, Agent, or Firm* — Cozen O'Connor

(57) ABSTRACT

An apparatus for measuring a hydrocarbon concentration of a gas stream in a line includes at least one sensor for measuring a hydrocarbon concentration, the position of said sensor being set off in relation to the line.

12 Claims, 2 Drawing Sheets

APPARATUS FOR MEASURING A HYDROCARBON CONCENTRATION AND INTERNAL COMBUSTION ENGINE

PRIORITY CLAIM

This is a U.S. national stage of Application No. PCT1EP2009/061306, filed on Sep. 2, 2009, which claims priority to German Application No: 10 2008 045 322.6, filed: Sep. 2, 2008, the contents of which are incorporated herein by reference.

BACKGROUND OF THE INVENTION

1. Field of the Invention

The invention relates to an arrangement for measuring a hydrocarbon concentration and to an internal combustion engine apparatus having such an arrangement.

2. Related Art

Exhaust gases released from the fuel can escape from the fuel tank of a motor vehicle in which, for example, gasoline is stored. At high outside temperatures or due to vibrations of the fuel tank during travel, highly volatile hydrocarbons can be released from the fuel and can leave the fuel tank as a gas. In order to counter this, fuel tanks can be closed in a gastight manner. The volatile hydrocarbons are then stored temporarily in a storage reservoir and can be fed to the intake air of the internal combustion engine. If the quantity of hydrocarbons released in the intake air it is not known, or is not known sufficiently accurately, the extent to which the quantity of fuel injected has to be reduced in order to achieve as optimum an air/fuel ratio as possible cannot be accurately controlled. This leads to an increased fuel consumption of the internal combustion engine and possibly also to poorer emission values.

SUMMARY OF THE INVENTION

An object of one embodiment of the invention is to specify an arrangement for measuring a hydrocarbon concentration and an internal combustion engine apparatus that enables precise operation of an internal combustion engine apparatus.

An arrangement for measuring a hydrocarbon concentration of a gas flow in a line comprises at least one sensor for measuring a hydrocarbon concentration. The sensor is set back with respect to the line. As a result of this arrangement, the sensor can measure the hydrocarbon concentration in a manner isolated from the volumetric flow in the line.

In one embodiment, the hydrocarbon sensor is arranged in a sensor chamber coupled to the line. A gas-permeable element can be arranged between the line and the sensor chamber. This results in as simple a construction of a set-back sensor as possible.

The gas-permeable element can be so gas-permeable that the hydrocarbon concentration of the gas in the sensor chamber depends on the hydrocarbon concentration of the gas flow in the line. As a result, the hydrocarbon content determined by the sensor is representative of the hydrocarbon concentration of the gas flow in the line.

The gas-permeable element can be a barrier for flames. As a result, a fire that develops due to a malfunction at the sensor cannot spread in the line.

The at least one sensor can have at least one heating element for heating a gas flow and at least one temperature sensor. In a further embodiment, the at least one sensor can have at least one first and one second temperature sensor, wherein the at least one heating element is arranged between the first temperature sensor and the second temperature sensor. As a result of this construction, the hydrocarbon content can be determined relatively accurately. In a further exemplary embodiment, the sensor comprises at least one semiconductor component that is integrated in the at least one sensor and is set up for sending temperature-dependent signals.

An internal combustion engine apparatus comprises an arrangement for measuring a hydrocarbon concentration of a gas flow in a line as described above. Owing to the fact that the hydrocarbon concentration of the gas flow is known, the internal combustion engine apparatus can be controlled in a relatively precise manner. The line of the arrangement can be designed for pneumatic communication between a tank venting system and at least one cylinder of the internal combustion engine apparatus. The internal combustion engine apparatus can comprise a storage reservoir for storing gaseous hydrocarbons, said storage reservoir being coupled to the line.

BRIEF DESCRIPTION OF DRAWINGS

Further features, advantages and developments follow from the examples below explained in conjunction with FIGS. 1 to 3. In the drawings.

DETAILED DESCRIPTION OF THE DRAWINGS

Figure 1:
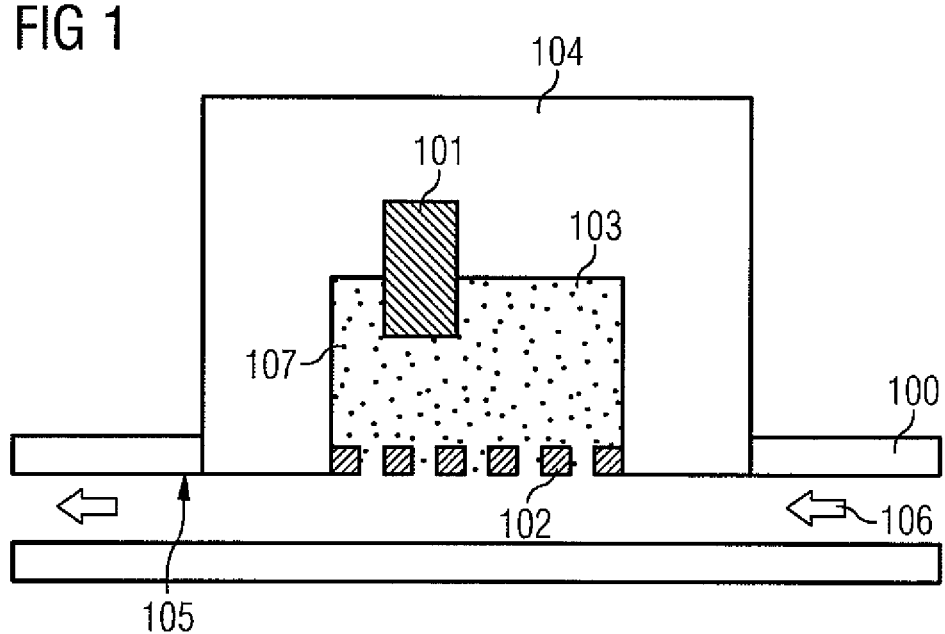
FIG. 1 is a schematic arrangement of a sensor in a sensor chamber.

FIG. 1 shows a line 100 in which a gas flow 106 flows. Coupled to the line 100 is a housing 104 that surrounds a sensor chamber 103. The housing 104 is coupled to the line 100 in such a way that the gas that moves in the line 100 can pass at least partly into the sensor chamber 103. Hydrocarbons 107 are located in the sensor chamber. A sensor 101, which is set up for measuring a hydrocarbon concentration, is arranged in such a way that the sensitive regions thereof are arranged in the sensor chamber 103 or can come into contact with the hydrocarbons 107. A gas-permeable element 102 is arranged on the sensor chamber 103 in the direction of the line 100.

The line 100, which, for example, is part of a tank venting system of an internal combustion engine apparatus, can be coupled with one end to a tank for gaseous hydrocarbons. The gas flows from this tank, for example to an intake side of an internal combustion engine. The gas flows through the line 100. Owing to the fact that the sensor 101 is set back with respect to the line 100, the gas at the sensor has a lower flow velocity or possibly no flow velocity. The sensor can measure the hydrocarbon concentration in a manner isolated from the flow velocity of the gas flow 106.

The sensor chamber 103 is surrounded by the housing 104 in such a way that the chamber volume is so minimal that a change in the hydrocarbon concentration in the line 100 results in as rapid a change in the hydrocarbon concentration in the sensor chamber 103 as possible. The gas exchange takes place more quickly with a smaller volume of the sensor chamber 103. The hydrocarbon concentration in the sensor chamber 103 is as far as possible the same as the hydrocarbon concentration in the line 100.

The gas-permeable element 102 is arranged between the sensor chamber 103 and the line 100. In one embodiment, the gas-permeable element 102 is a grid. At least some of the gas which is conducted in the line 100 can pass through the grid 102 into the sensor chamber 103. Gas which is in the sensor chamber 103 can pass into the line 100. The grid 102 is designed in such a way that it constitutes a barrier for flames. Hydrocarbons can be ignited in the sensor chamber 103 due to a malfunction, for example a short circuit at the sensor 101. The flames of this combustion cannot overcome the grid 102. The combustion therefore cannot spread inside the line 100 and is extinguished as soon as all the hydrocarbons 107 in the sensor chamber 103 are burned.

With respect to the environment, the line 100 has an inner side 105 which in operation is oriented at the top with respect to the gravitational force. The housing 104 and the sensor chamber 103 are arranged on this inner side 105. The sensor chamber 103 lies above the line 100, such that as far as possible no liquid can penetrate into the chamber, for example due to gravitational force. The sensor 101 is arranged in the chamber in such a way that a good gas exchange can take place between the sensor chamber 103 and the line 100 and the movement of the gas within the sensor chamber 103 is as small as possible at the sensor 101.

The sensor 101 has, for example, a heating element for heating the gas and a temperature sensor. For example, the sensor is arranged on a silicon chip. The gas containing hydrocarbons is heated, and the thermal conductivity of the gas can be determined with the aid of signals from the temperature sensor. The concentration of the hydrocarbons can be determined therefrom. The sensor can comprise an evaluating circuit and/or a digital-analog converter and/or further elements. In a further embodiment, the sensor comprises a component which works in a temperature-dependent manner, for example an NTC thermistor (negative temperature coefficient thermistor) or a diode.

Figure 2:
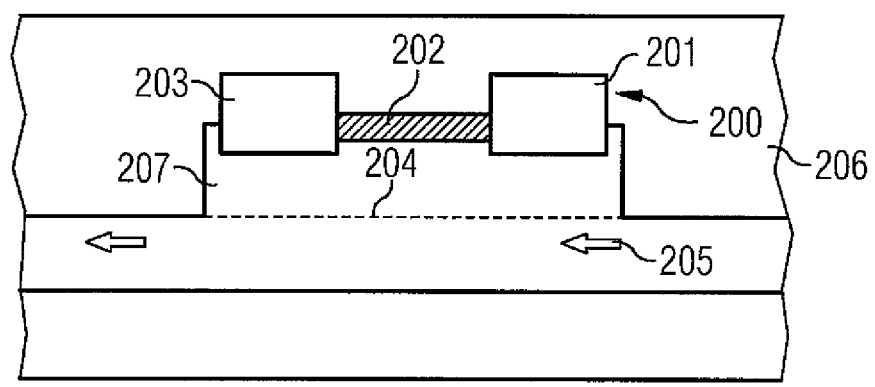
FIG. 2 is a schematic illustration of a sensor according to one embodiment.

FIG. 2 shows a sensor 200 which is set back with respect to a line 206. The sensor 200 has a temperature sensor 201 and a further temperature sensor 203 which are arranged on each side of a heating element 202. The sensor 200 is set up for measuring the concentration of hydrocarbon in the gas 205. The sensor 200 is arranged in a sensor chamber 207 that is isolated from the line by a grid 204. The gas has as low a flow velocity as possible in the sensor chamber 207.

The sensor 200 is integrated, for example, on a silicon substrate and can comprise further components, for example an evaluating circuit, an analog-digital converter or a circuit for temperature compensation. The temperature sensor 201 and the temperature sensor 203 can each have a plurality of temperature probes for measuring a temperature. The temperature sensors 201 and 203 and the heating element 202 are arranged in one plane.

The temperature sensor 201 measures a first temperature and the temperature sensor 203 measures a further temperature. The respective level of the temperatures results from the heating of the gas by the heating element 202. Depending on the hydrocarbon concentration, the gas is heated to a varying degree at a constant heating capacity. The temperature measured by the sensor 201 and the further temperature measured by the temperature sensor 203 can be added for evaluation. This value of the added temperatures, on the basis of a known heating capacity, is representative of the hydrocarbon concentration of the gas in the sensor chamber 207. Owing to the fact that as good a gas exchange as possible between the sensor chamber 207 and the line 206 can take place, this value is also representative of the hydrocarbon concentration of the gas 205.

Figure 3:
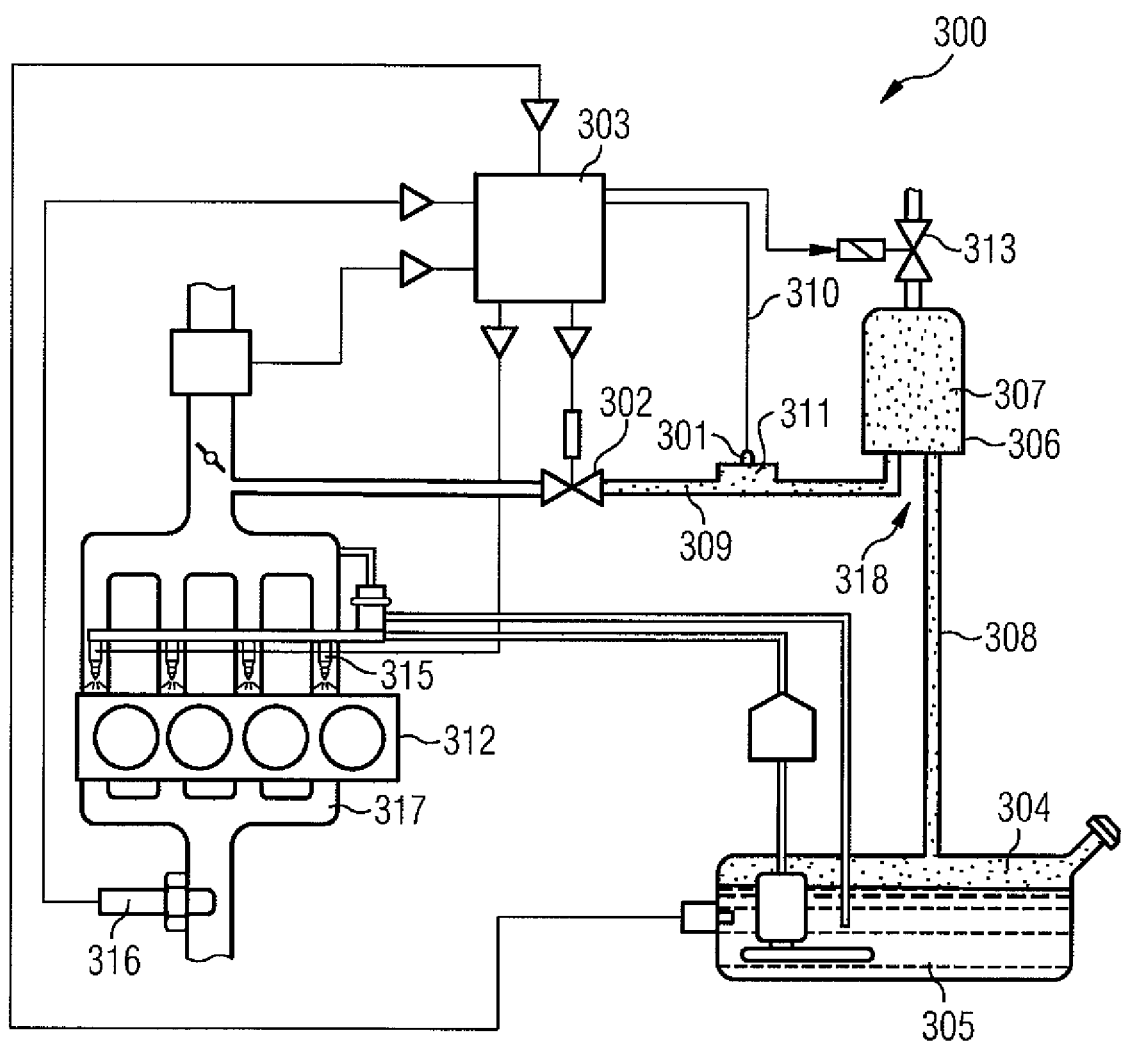
FIG. 3 is a schematic illustration of an internal combustion engine apparatus.

FIG. 3 shows an internal combustion engine apparatus 300. The internal combustion engine apparatus 300 has a fuel tank 304, an internal combustion engine 312 and a tank venting system 318. Fuel 305, for example gasoline, is stored in the fuel tank 304. Gaseous hydrocarbons 307 which are released from the liquid fuel 305 are fed to the internal combustion engine 312 via the tank venting system. The tank venting system 318 has a line 308 which is coupled to the fuel tank 304 and a hydrocarbon tank 306. Gaseous hydrocarbons can be directed into the hydrocarbon tank 306 from the fuel tank 304. The hydrocarbon tank is coupled to the internal combustion engine 312, in particular to the intake tract of the internal combustion engine, via a line 309.

A sensor 301 for measuring a hydrocarbon concentration is set back on the line 309. A sensor chamber 311, in which the sensor 301 is arranged, is coupled to the line 309. A grid, which in particular constitutes a barrier for flames, can be arranged between the sensor chamber 311 and the line 309. Further sensors for measuring a hydrocarbon concentration can also be arranged. For example, sensors which are set up for measuring a hydrocarbon content of a gas are arranged on the line 308. The sensor 301 is coupled to an engine controller 303 via an electric line 310. The engine controller 303 can evaluate signals from the sensor 301 and determine the hydrocarbon concentration in the sensor chamber 311.

The gas flow through the line 309 can be controlled by a valve 302 coupled to the line 309. The valve 302 is coupled to the engine controller 303 via an electric line. The engine controller 303 can evaluate the signals from the hydrocarbon sensors 301 and can control valves 302, 313.

By a fuel delivery unit, the fuel 305 can be delivered via fuel lines to the internal combustion engine 312, where it is injected via at least one injection valve 315 into the intake tract of the internal combustion engine or into at least one cylinder and is burned in the combustion engine. The exhaust gases of the combustion process are conveyed away from the engine through an exhaust gas system 317. Arranged in the exhaust gas system 317 is a Lambda probe 316, which can determine an air-to-fuel ratio. To this end, the Lambda probe 316 measures the residual oxygen content in the exhaust gas.

Hydrocarbons, for example methane, butane or propane, evaporate from the fuel 305. The various hydrocarbon chains have different evaporation temperatures, and therefore, depending on the outside temperature, different hydrocarbons are released from the liquid fuel 305. The higher the outside temperature and thus the higher the temperature of the fuel 305, the greater the amount of hydrocarbons that are transformed into the gas phase. The tank 304 in which the fuel 305 is stored is designed to be gastight, such that as far as possible no gas can inadvertently escape from the tank 304. To this end, the tank cap closes a filler neck of the fuel tank as far as possible in a gastight manner. The gas mixture which contains hydrocarbons and forms in the tank 304 is directed into the hydrocarbon tank 306 via the line 305.

The hydrocarbon tank 306 can contain an activated carbon storage element. The evaporated hydrocarbons 307 are absorbed by the activated carbon, stored and released again when required. When the hydrocarbon tank 306 has received a certain quantity of hydrocarbons, it can be emptied via the line 309. To this end, air that absorbs the hydrocarbons is blown into the hydrocarbon tank 306 from outside via a valve 313. The air containing hydrocarbon can be used as intake air for the internal combustion engine 312 and can thus contribute to the combustion in the engine 312.

Since a certain quantity of energy is supplied to the internal combustion engine 312 by the hydrocarbons in the intake air, correspondingly less fuel can be injected via the injection valves 315. To control this ratio, the hydrocarbon content of the fed air can be measured via the hydrocarbon sensors.

Owing to the fact that the hydrocarbon sensor 301 in the sensor chamber 311 is set back with respect to the line 309, said sensor 301 measures only the hydrocarbon concentration of the gas in a manner isolated from the mass flow through the line 309. The mass flow can be determined by the engine controller 303 by stored models that simulate the mass flow through the line 309 or the valve 302. It can also be determined directly by one or more air mass sensors; however, it can also be partly derived from other measured quantities by corresponding models.

The engine controller 303 evaluates the signals from the sensor 301, such that the concentration of hydrocarbons of the gas flow through the line 309 is known. The mass flow is known on account of the engine characteristics maps stored in the engine controller 303. The amount of energy in the form of gaseous hydrocarbons that is supplied to the internal combustion engine 312 is therefore known. The engine controller 303 correspondingly controls actuators, such that the ratio of liquid fuel to gaseous hydrocarbons is as optimum as possible and as a result the fuel consumption is as low as possible. As a result, there is likewise as low a level of emission of the exhaust gases as possible.

The activated carbon filter can be emptied relatively quickly, since the controller works relatively quickly, in particular compared with a controller based on data from the Lambda sensor 316. The quantity of fuel which is injected into the internal combustion engine via the injection valves 315 is controlled not only on the basis of the data from the Lambda sensor but also directly by data which the engine controller 303 determines by the hydrocarbon sensors 301. The quantity of gas which flows through the line 309 need not be limited, which in particular leads to relatively short regeneration times of the hydrocarbon tank 306. This can be advantageous in vehicles having hybrid drive or a start-stop technique, in which a shorter engine running time necessitates quick emptying of the activated carbon filter 306.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An arrangement for measuring a hydrocarbon concentration of a gas flow in a line, comprising:
   at least one hydrocarbon sensor configured to measure a hydrocarbon concentration, the hydrocarbon sensor being arranged in a sensor chamber coupled to the line and being set back in the sensor chamber with respect to the line, the hydrocarbon sensor comprising:
   at least one first temperature sensor;
   at least one second temperature sensor; and
   at least one heating element for heating the gas flow arranged between the at least one first temperature sensor and the at least one second temperature sensor.

2. The arrangement as claimed in claim 1 further comprising a gas-permeable element arranged between the line and the sensor chamber.

3. The arrangement as claimed in claim 2, wherein the gas-permeable element is so gas-permeable that a hydrocarbon concentration of the gas in the sensor chamber depends on the hydrocarbon concentration of the gas flow in the line.

4. The arrangement as claimed in claim 3, wherein the gas-permeable element is configured as a flame barrier.

5. The arrangement as claimed in claim 2, wherein the gas-permeable element is configured as a flame barrier.

6. The arrangement as claimed in one of claim 5, wherein the at least one hydrocarbon sensor has at least one semiconductor component integrated in the at least one hydrocarbon sensor configured to send temperature-dependent signals.

7. The arrangement as claimed in claim 6 further comprising a gas-permeable element arranged between the line and the sensor chamber.

8. The arrangement as claimed in claim 7, wherein the gas-permeable element is configured as a flame barrier.

9. The arrangement as claimed in claim 1, wherein the at least one sensor has at least one semiconductor component integrated in the at least one sensor configured to send temperature-dependent signals.

10. An internal combustion engine apparatus comprising:
    an internal combustion engine; and
    an arrangement for measuring a hydrocarbon concentration of a gas flow in a line, comprising:
    at least one hydrocarbon sensor configured to measure a hydrocarbon concentration, the hydrocarbon sensor being arranged in a sensor chamber coupled to the line and being set back in the sensor chamber with respect to the line, the hydrocarbon sensor comprising:
    at least one first temperature sensor;
    at least one second temperature sensor; and
    at least one heating element for heating the gas flow arranged between the at least one first temperature sensor and the at least one second temperature sensor.

11. The internal combustion engine apparatus as claimed in claim 10, wherein the line is configured to provide pneumatic communication between a tank venting system and at least one cylinder of the internal combustion engine.

12. The internal combustion engine apparatus as claimed in claim 11 further comprising: a storage reservoir coupled to the line and configured to store gaseous hydrocarbons.

* * * * *